United States Patent
Lee et al.

(10) Patent No.: US 8,632,471 B2
(45) Date of Patent: Jan. 21, 2014

(54) PULSIMETER SENSOR USING HALL DEVICE

(76) Inventors: Sang Suk Lee, Wonju-si (KR); Sang Dae Choi, Suwon-si (KR); Myoung Chone An, Wonju-si (KR); Young Kuen Choi, Anseong-si (KR); Ki Wang Kim, Dobong-gu (KR); Dal Ho Park, Wonju-si (KR); Do Gwun Hwang, Wonju-si (KR); Soo Yong Ahn, Wonju-si (KR); Mi Sun Kim, Sokcho-si (KR); Hyun Sook Lee, Wonju-si (KR); Hyeon Ho Kim, Gwangjin-gu (KR)

( * ) Notice: Subject to any disclaimer, the term of this patent is extended or adjusted under 35 U.S.C. 154(b) by 1028 days.

(21) Appl. No.: 12/310,640

(22) PCT Filed: Feb. 20, 2007

(86) PCT No.: PCT/KR2007/000883
§ 371 (c)(1),
(2), (4) Date: Mar. 2, 2009

(87) PCT Pub. No.: WO2008/026809
PCT Pub. Date: Mar. 6, 2008

(65) Prior Publication Data
US 2010/0179440 A1 Jul. 15, 2010

(30) Foreign Application Priority Data
Sep. 1, 2006 (KR) .................. 10-2006-0084402

(51) Int. Cl.
*A61B 5/02* (2006.01)
(52) U.S. Cl.
USPC .......................... 600/500; 600/502

(58) Field of Classification Search
None
See application file for complete search history.

(56) References Cited

U.S. PATENT DOCUMENTS

| | | | |
|---|---|---|---|
| 2003/0212335 A1 | 11/2003 | Huang | |
| 2004/0210289 A1* | 10/2004 | Wang et al. | 607/116 |
| 2004/0251507 A1 | 12/2004 | Nakamura et al. | |

FOREIGN PATENT DOCUMENTS

| | | |
|---|---|---|
| KR | 2001-0028668 | 4/2001 |
| KR | 2002-0096224 | 12/2002 |
| KR | 20-0358195 | 7/2004 |
| KR | 10-2006-0071597 | 6/2006 |

OTHER PUBLICATIONS

Choi, et al., "Achievement of 3-D Pulse Diagnostic Apparatus by using Multi-Hall Devices"—Journal of Korean Magnetics Society, vol. 16, No. 4, Aug. 2006.

* cited by examiner

*Primary Examiner* — Benjamin P Blumel
(74) *Attorney, Agent, or Firm* — Gerald E. Hespos; Michael J. Porco; Matthew T. Hespos

(57) ABSTRACT

The present invention relates to a noninvasive medical pulsimeter sensor using a hall device. By forming a pulse-sensing part array with a hall device as a magnetic sensor, over the skin-contacting part which consists of a magnetic material, the present invention increases the integrity of sensors, enables to understand the spatial characteristics of the pulse which cannot be determined by the conventional pressure sensors, minimize the time for searching the pulse, and is applicable widely to portable pulsimeters and the likes.

20 Claims, 5 Drawing Sheets

PULSIMETER SENSOR USING HALL DEVICE

BACKGROUND OF THE INVENTION

1. Field of the Invention

The present invention relates to a pulsimeter sensor using a hall device, and more particularly to a medical pulsimeter sensor, wherein a pulse-sensing part array consists of a hall device and the pulse-sensing part array is located over a skin-contacting part which consists of a magnetic material. When a radial pulse transferred to the magnetic material of the skin-contacting part results in changes in a magnetic field of the lower part of the pulse-sensing part array, these changes in the magnetic field can be detected by the hall device of the pulse-sensing part array. Finally, according to the present invention, the radial pulse can be measured noninvasively by detecting the changes of the magnetic field.

2. Description of the Related Art

Currently, most medical detecting sensors for the pulse are the invasive sensors, which detect the changes in the blood pressure by injecting tubes into the blood vessels, or the noninvasive sensors using pressure sensors.

Particularly, the pulsimeter sensor using pressure sensors has been researched many times due to its noninvasivity and the Korean Patent Publication Number 10-2001-0028668 regarding the medical pulsimeter sensor, the Korean Patent Publication Number 10-2002-96224 regarding the automatic pulsimeter, and the Korean Utility Registration Number 20-0358195 regarding the pulse wave measuring device et al. are some examples.

In the Korean Patent Publication Number 10-2001-28668, as shown in FIG. 1, the medical pulsimeter sensor includes a pressure-sensing sensor 4 including a silicon layer 1, which is adhered closely to the upper skin at the radial artery and close up the air layer tight to sense the pressure change of the air layer depending on the vibration of a pulse wave, a silicon gel 2, which transfers the pressure change of the air layer, and a pressure-measuring plate 3, which measures the pressure changes to be transferred by the silicon gel; a silicon gum 5, having a hole fit for the pressure-sensing part, wrapping the pressure-sensing part and being adhered to the front side of the pressure-sensing sensor 4 and making the pressure-sensing sensor 4 fixed to the skin of the examinee; and a fortified plastic plate 6, being adhered to the back side to the pressure-sensing sensor 4, and transferring the variable pressure from the back side of the pressure-sensing sensor 4 to the skin of the examinee.

The silicon layer 1 and the silicon gel 2, which are in front of the pressure-measuring plate 3, eliminate a cold feeling and unnecessary stimulus of metals, of which the conventional pulse-sensing part is comprised. However, the conventional pulsimeter sensor using pressure sensors has the problems that it unnecessarily closes up the air layer tight, transfers the pressure changes indirectly to a pressure-measuring plate and is unable to measure the exact pulse. And it is impossible to search for the location of the pulse depending on each person and measure an exact pulse quickly with the conventional pulsimeter sensor using pressure sensors.

By the way, Oriental medical doctors have diagnosed the three pulse locations on the wrist, over the radial artery classified as Chon, Gwan and Cheok. The "Gwan" is located on the coronal process of the radial artery on the wrist, the "Chon" is located on the spot 1~1.3 cm from the Gwan toward a palm of the hand, and the "Cheok" is located on the spot 1~1.3 cm from the Gwan toward an elbow. The doctor places the index, middle and ring fingers on the examinee's the Chon, Gwan and Cheok with three different degrees of pressing, that is, moderate (the "Bu" state), hard (the "Jung" state), and light (the "Chim" state).

To improve problems which the conventional pulsimeters have, the Korean Patent Publication Number 10-2002-96224 regarding the automatic pulsimeter, disclosed invention about mechanical embodiments of the way Oriental medical doctors feel the pulse with one pressure sensor and the Korean Utility Registration Number 20-0358195 regarding the pulse wave measuring device disclosed invention measuring the three regions of Chon, Gwan, and Cheok simultaneously with three pressure sensors.

However, the conventional arts use pressure sensors such as a piezoelectric device, and have the following problems:

First, it is possible to understand the time characteristics to some extent by measuring the changes in the pulse pressure (wave form) with the pressure sensors, but it is hard to understand the spatial characteristics (three-dimensional configurations) of the pulse such as the depth, the area, the length of the pulse and so on, which have been recognized more important in the traditional pulse diagnosis.

Accordingly, as shown in FIG. 2, only 7 qualities, those are related with the time characteristics, in words, slow pulse, rapid pulse, slippery pulse, uneven pulse, abrupt pulse, knotted pulse, and regularly intermittent pulse, can be understood by the conventional arts among 28qualities that have been used in traditional pulse diagnosis. Therefore, there has been a limitation on replacing the traditional pulse diagnosis by examiners with these mechanical pulsimeters.

Second, products using the pressure sensors to understand the spatial characteristics of the pulse have been manufactured recently, but there is a limitation on the degree of integrity for pressure-sensors. Therefore, there is nothing but to get minimum spatial information about the pulse through an excess interpolation.

Third, to measure the spatial characteristics of the pulse properly, sensors should find out the location of the radial artery accurately. However, only several pressure sensors cannot search the center of the radial artery properly, and it takes too long to search the locations of the pulses.

Fourth, because of the nature of the pressure sensors of having a weakness in movement noises, it is impossible to measure pulses with wearing themselves, and this characteristic has an application limit to a portable apparatus.

Lastly, most pressure sensors have been equipped with measuring means of a rigid body, and applying pressure on measurement of a pulse generates a pain.

SUMMARY OF THE INVENTION

To solve the problems which the conventional pulsimeter sensors have, the present invention is directed to a pulsimeter sensor using a hall device.

To achieve the objectives of the present invention, a pulsimeter sensor is characterized by comprising a skin-contacting part 10, formed with a magnetic material to be contacted to a skin to examine the pulse; a pulse-sensing part 20, located some distance over the skin-contacting part and formed as an array type with at least one hall device 21; and a spatial part 30, located between the skin-contacting part 10 and the pulse-sensing part 20, as shown in FIG. 3.

The present invention embodies a pulse-sensing part of an array type using a hall device as a minute unit cell. As a result, it is possible to minimize the time to search for the locations of the pulse, measure the pulse which the conventional pressure sensors could not measure, and understand the spatial characteristics of the pulse completely. Therefore, it is possible to search for all 28 qualities of the traditional pulse diagnosis according to the present invention.

Also, a hall device as a magnetic sensor can be diminished in size by a semiconductor lithography process, it has little measuring fault according to the movements of the examinee, and it is possible to design various applications such as wrist watches, rings and IC chips as a wearable (portable) pulsimeter.

Furthermore, while the conventional pulsimeters using pressure sensors have a problem to generate a pain by applying a pressure into a skin, the present invention receives the pulse through a soft magnetic material of a skin-contacting part, and it does not generate a pain.

BRIEF DESCRIPTION OF THE DRAWINGS

The invention may be better understood by the drawings that are briefly described below and attached hereto, in the several figures of which identical reference numbers (if any) refer to identical or similar elements.

Figures 1, 2:
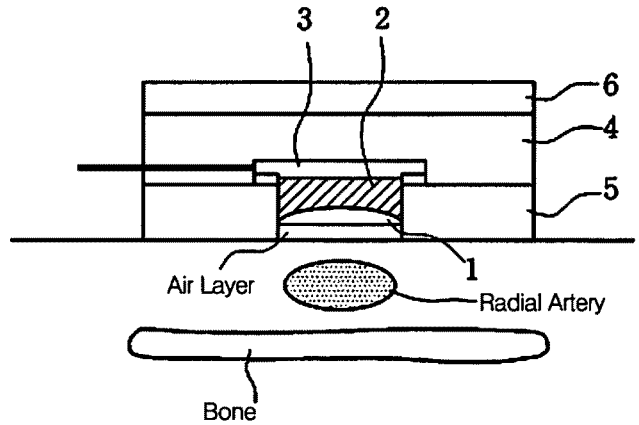
FIG. 1 is a cross-section of a conventional pulsimeter sensor.
FIG. 2 shows pulse characteristics seen in a traditional pulse diagnosis.
Figure 3:
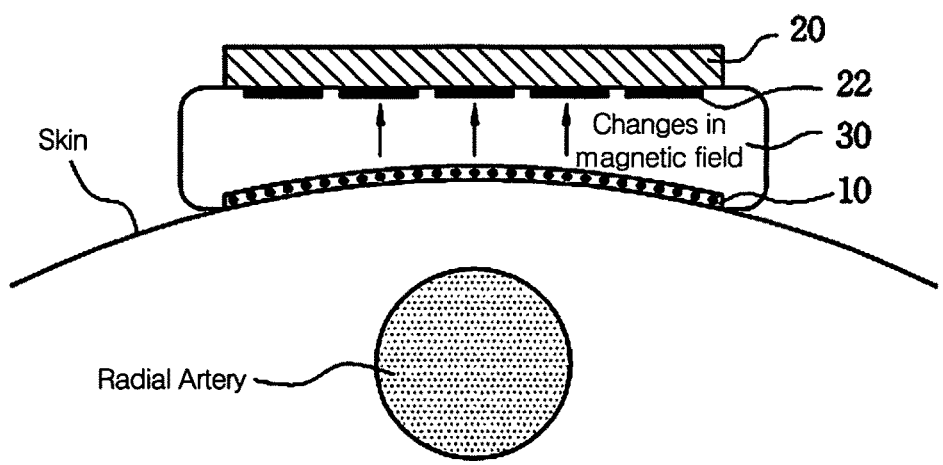
FIG. 3 is a cross-section of one embodiment of a pulsimeter sensor of the present invention.

In these drawings, the following reference numbers are used throughout: reference number 10 indicates a skin-contacting part, 20 means a pulse-sensing part, 21 means a hall device, 23 means a multi-channel voltage detector circuit, 25 means a multiplexer, 27 means a microprocessor, 29 means a communication driver, and 30 means a spatial part.

DETAILED DESCRIPTION OF THE PREFERRED EMBODIMENTS

A detailed description of preferred embodiments of the present invention is provided below with respect to the accompanying drawings.

A magnetic material of a skin-contacting part 10 of the present invention can be submicron magnetic nano-particles like magnetic nano-beads or ultra thin magnetic films, comprised of small permanent magnets, of which their locations can be changed easily depending on the vibration of the pulse. More specifically, it is more preferable that the magnetic material comprises a nano-bead type nano-magnetic particle of 10~100 nm in diameter or a disk magnet of 1~3 mm in diameter and 0.3~1 mm in thickness.

Also, it is preferable that the nano-magnetic particle and the disk magnet comprise at least one selected from the group consisting of Nd, Co, $Fe_3O_4$ and $Fe_2O_3$. As a Nd—Fe—B magnet, which includes Nd, one of rare earth metals, and is manufactured by power metallurgy of Nd and B and polishment, has highest magnetic quality of magnetic materials and shows excellent magnetic quality with only small quantity, it is more preferable to use a Nd—Fe—B magnet.

The magnetic material of the skin-contacting part should be adhered to a skin and move easily according to the vibration of the pulse. Therefore, it is preferable that the magnetic material is as ultra-thin as 1 mm and less. It is more preferable that the magnetic material is a flexible ribbon-type magnetic pad. In a case of using the ribbon-type magnetic pads for a magnetic material, magnets of 200~300 Oe at a 3 mm distance are preferable, however, it will be good to determine the magnetic field strength according to the magnetism sensitivity of a hall device. For one embodiment using a hall device with the magnetism sensitivity of 2.5 mV/Oe, we could detect the pulse fully with a magnetic material of 200 Oe at a 1 mm distance.

The size of the ribbon-type magnetic pads is determined by the pulse-sensing part 20, and for example, the ribbon type magnetic pads can be shaped with 5 stripes, of which a stripe is 1.0 mm×12 mm. In this instance, there is an advantage that it is possible to fix the skin-contacting part 10 with grooves which were made by stripes of the magnetic pads.

Especially, it is preferable that the skin-contacting surface of the skin-contacting part 10 is made of soft materials not to press skin.

Next, an unit cell 21 of the pulse-sensing part can use a hall device. Many researches in hall devices for detecting magnetic fields have been already investigating (Refer to Korean Patent Application Publication Number 10-2004-64263 and others). Therefore, matters relevant to the present invention only are described here briefly.

In the present invention, a hall device used as an unit cell 21 uses Hall effect. Hall effect refers to the phenomenon when an electric current flows through a conductor in a perpendicular magnetic field, a electric field perpendicular to the electric current flow and the magnetic field is generated. Therefore, a hall device in the present invention requires two sensing terminals (current input terminal and output terminal) and two measuring terminals (hall voltage measuring terminal).

The Hall voltage $V_H$ measured by a hall device can be expressed as the following Equation 1 (Refer to the Korean Application Publication Number 10-2004-64263).

$$V_H = (G \times r_H \times I \times B_Z)/(n \times e \times t) \quad \text{[Equation 1]}$$

where G is an geometrical factor regarding the size of a hall device, $r_H$ is a hall scattering factor, I is a sensing current, $B_Z$ is an applied magnetic flux density, n is a carrier density, e is an unit charge, and t is a thickness of layer in which sensing current flows.

According to Equation 1, when only the magnetic flux density $B_Z$ is changed under the same condition, the hall voltage $V_H$ is also changed according to the degree of the $B_Z$ change. By measuring the hall voltage $V_H$, one can determine changes in the magnetic field $B_Z$. Therefore, one can determine the movement of the magnetic material of the skin-contacting part and understand the pulse.

Figure 4:
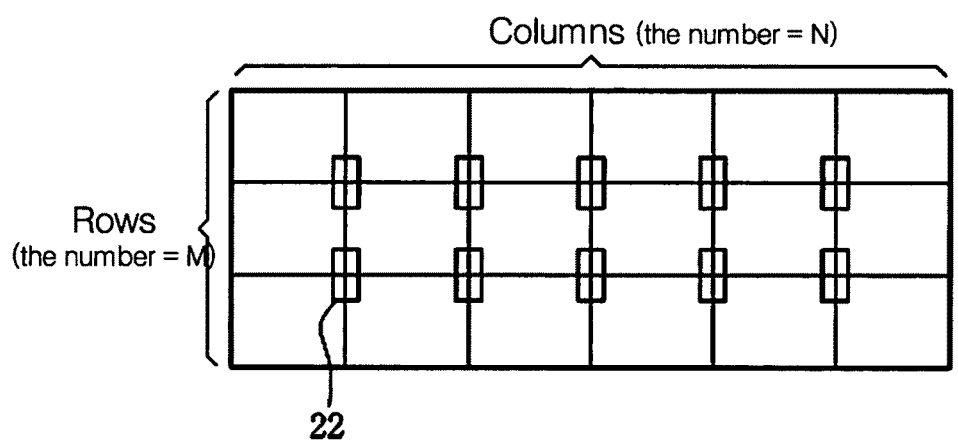
FIG. 4 is one embodiment of a pulse-sensing part array.

Therefore, a pulse-sensing part 20 of the present invention, which uses the hall device as an unit cell 21, is arranged in an array type, as shown in FIG. 4.

Array types can be embodied variously according to the objective of the pulse measurement and it is preferable that in order to get all pulse qualities by the traditional pulse diagnosis, the pulse-sensing part array is formed by dividing unit cells into three groups corresponding to "Chon", "Gwan", and "Cheok", arranging each group of unit cells as 2×5 or 3×6 matrix array and packaging.

The unit cell 21 of the pulse-sensing part 20 can be various in sizes depending on the process technology and the degree of the integration and it is preferable that the package size of each region is about as 1.0 cm×2.0 cm as finger size.

After all, the present invention is characterized by arranging minute unit cells 21 of the pulse-sensing part 20 appropriately, and therefore it is possible to understand not only the time characteristics of the pulse by a pulse wave measurement, but also the spatial characteristics of the pulse fully by a measurement of widths, lengths, degree of palpation of the pulse and so on.

On one side of the pulse-sensing part, a voltage detecting circuit for a hall voltage detected from the each hall device can be comprised. It is preferable that the voltage detecting circuit comprises a differential circuit for detecting only changes in the hall voltage, that is, changes in the magnetic field. Also, it is preferable that the voltage detecting circuit further comprises a noise filter for removing noise generated by the movement on measuring the pulse, a signal amplifier and an output attenuator.

Figure 5:
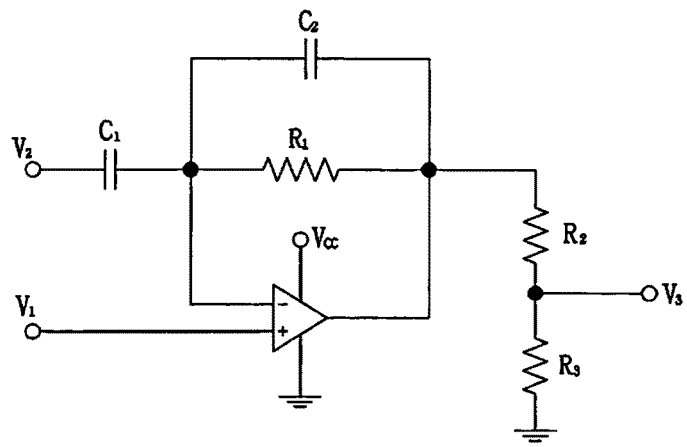
FIG. 5 is one embodiment of a voltage detector circuit.

FIG. 5 illustrates one embodiment of the voltage detecting circuit.

In FIG. 5, operational amplifier, capacitor $C_1$ and resistance $R_1$ function as a differential circuit, capacitor $C_2$ and resistance $R_1$ function as a noise filter, resistance $R_1$ functions as a signal amplifier, and resistance $R_2$ functions as an output attenuator. $V_1$ and $V_2$ are connected to each measuring terminal (hall voltage measuring terminal) and $V_3$, an output terminal, is connected to other block of the voltage detecting circuit.

Figure 6:
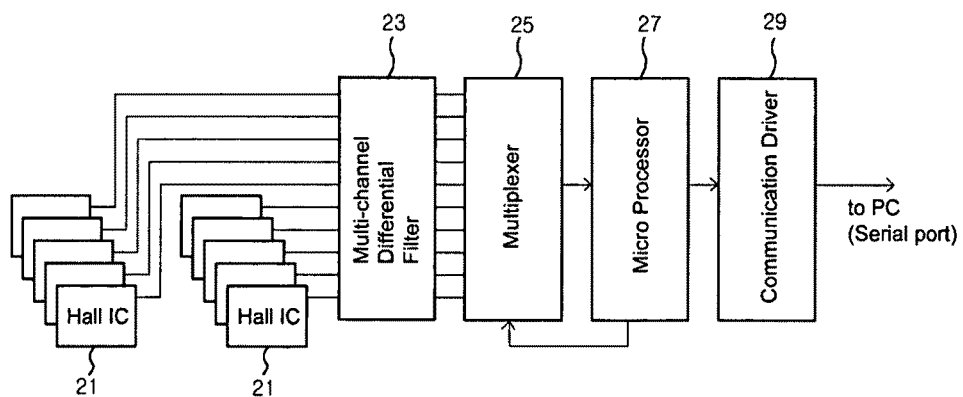
FIG. 6 is a block diagram showing a detected signal treatment hardware which is built in a pulse-sensing part.

Therefore, as shown in FIG. 6, the pulse-sensing part has output terminals ($V_3$) as many as the number of hall devices inside and it has a multi-channel voltage detecting circuit 23.

The pulse-sensing part further comprises a multiplexer 25 which receives multi-signals from the multi-channel voltage detecting circuit 23 and selects one signal; a microprocessor 27 which controls the multiplexer in such a way that the microprocessor receives each signal from the multiplexer and makes it a packet with a predetermined resolution and transfers it; and a communication driver 29 which transfers the packet digital signal input by the microprocessor to an outer image processor in a single body.

It is preferable that a spatial part 30 is a pressure chamber, which maintains a predetermined constant pressure, or is filled with soft pads. In the present invention, a spatial part 30 functions to keep a predetermined space between the skin-contacting region 10 and the pulse-sensing part 20 and to transfer changes in the magnetic field by the magnetic material of the skin-contacting part 10 to the pulse-sensing part 20 as it is. Therefore any means can be used in the present invention if it can keep a predetermined space and transfer changes in the magnetic field by the magnetic material of the skin-contacting part 10 to the pulse-sensing part 20 as it is.

A distance between the skin-contacting part and the pulse-sensing part of the spatial part 30 can be determined based on the magnetic strength of the magnetic material of the skin-contacting part 10 and magnetism sensitivity of the unit cell 21 of the pulse-sensing part 20. If the magnetic material of the skin-contacting part 10 is a ribbon-type magnetic pad, of which magnetic strength is 200~300 Oe, it is preferable that the distance is maintained as 1~3 mm.

Furthermore, when a pressure controlling apparatus is adhered to the pressure chamber, it is possible to get pulse qualities easily at the state of "Bu", "Jung", and "Chim" of the traditional pulse diagnosis.

However, to show the function of the pressure controlling apparatus properly, it is necessary to embody the pulsimeter sensor according to the present invention into a wrist watch or a bracelet and transfer the increased pressure to the skin-contacting part 10 intact when pressure of the pressure chamber is increased.

In addition, a conventional pressure sensor can be adhered to the skin-contacting part 10, separately from the magnetic materials, and this can make up the functions that the pressure sensor only has.

Figure 7:
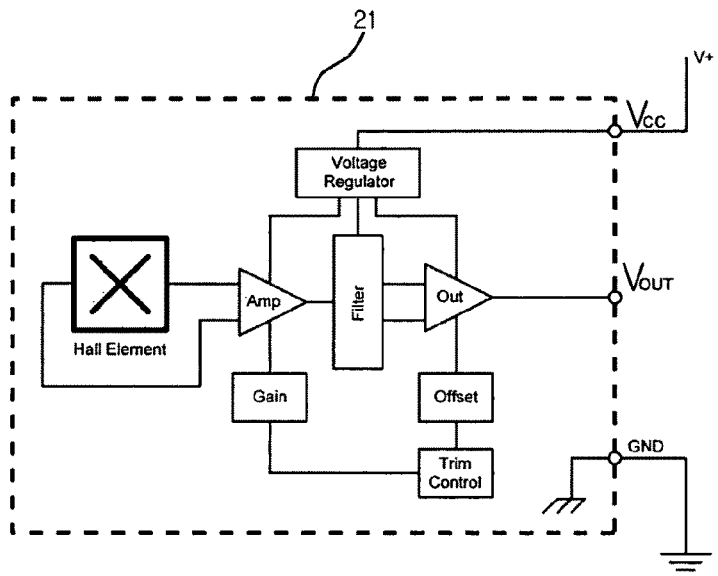
FIG. 7 is a functional block diagram for one embodiment of a hall device.
Figure 8:
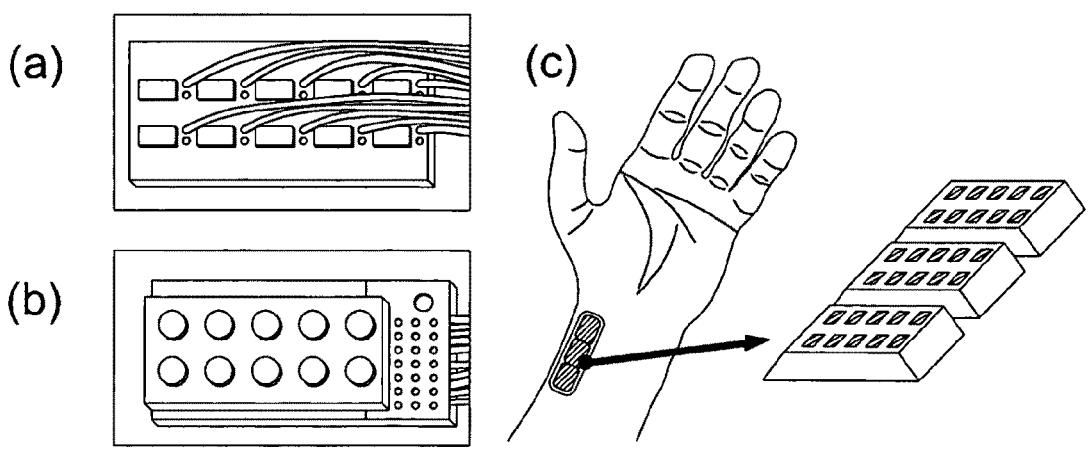
FIG. 8 is the photograph of one embodiment of a pulsimeter sensor using a hall device.

To actualize the embodiments and confirm their operating status, as shown in FIG. 7, we used ten hall devices having the functional block diagram of FIG. 7 and the magnetism sensitivity of 2.5 mV/Oe, arranged the pulse-sensing part 20 as shown in FIG. 8(a), structured the skin-contacting part 10 by arranging ten disk Nd magnets of 3 mm in diameter and 1 mm in thickness corresponding to the location of the each hall device, as shown in FIG. 8(b), filled up the space between the pulse-sensing part 20 and the skin-contacting part 10 with soft pads, and embodied the pulsimeter sensor using a hall device. The Nd magnet was about 200 Oe at a 1 mm from the central axis.

Figure 9:
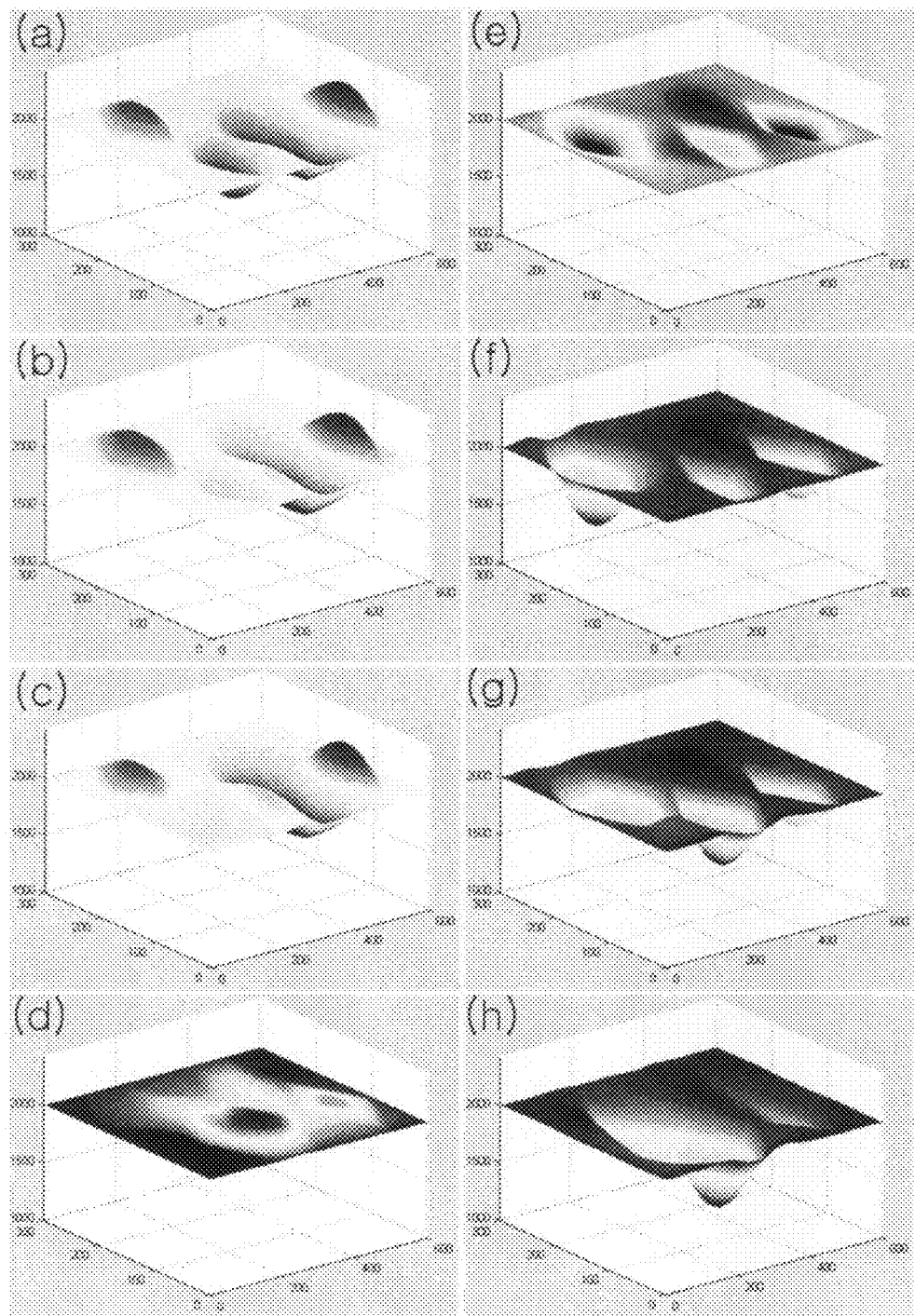
FIG. 9 is the computer-processed three-dimensional image of signals detected by the pulsimeter sensor of FIG. 8.

We measured signals at the "Chon", "Gwan" and "Cheok" region, as shown in FIG. 8(c) using the pulsimeter sensor, passed signals through the voltage detecting circuit as shown in FIG. 5, made a differential input, an automatic zero set, a noise filtering, a high power gain and output attenuation, output them with 12 bit resolution at 30 FPS, RS232C, simulated the result with a predetermined computer processing, and obtained three-dimensional image of FIG. 9.

So far, the preferable embodiments of the present invention have been described herein, but it will be evident that the present invention cannot be defined only by the described embodiments herein, and it will be understood that the invention herein described are generally applicable and executed as various modified embodiments by those skilled in the art. For example, materials and numerical values for a skin-contacting part 10, a pulse-sensing part 20 and a spatial part 30 can be various within the technical thought of the present invention.

The present invention relates to a noninvasive medical pulsimeter sensor using a hall device. By forming a pulse-sensing part array with a hall device, over the skin-contacting part, which consists of a magnetic material, the present invention increases the integrity of sensors, minimizes the time for searching the pulse, and is applicable widely to a portable pulsimeter and the like.

The invention claimed is:

1. A pulsimeter sensor using a hall device, comprising:
   a skin-contacting part, formed with a magnetic material to be contacted to a skin to examine the pulse;
   a pulse-sensing part, located some distance over the skin-contacting part and formed with at least one hall device; and
   a spatial part, located between the skin-contacting part and the pulse-sensing part.

2. The pulsimeter sensor of claim 1,
   wherein the magnetic material of the skin-contacting part comprises a nano-bead type nano-magnetic particle of 10~100nm in diameter or a disk magnet of 1~3mm in diameter and 0.3~1mm in thickness.

3. The pulsimeter sensor of claim 2,
   wherein the nano-magnetic particle and the disk magnet comprise at least one selected from the group consisting of Nd, Co, $Fe_3O_4$ and $Fe_2O_3$.

4. The pulsimeter sensor of claim 1,
   wherein the magnetic material of the skin-contacting part is as ultra-thin as 1mm and less.

5. The pulsimeter sensor of claim 4,
   wherein the untra-thin magnetic material of the skin-contacting part is a ribbon-type magnetic pad.

6. The pulsimeter sensor of claim 5,
   wherein the magnetic field strength of the ribbon-type magnetic pad is 200~300 Oe at a 3mm distance.

7. The pulsimeter sensor of claim 1,
wherein the pulse-sensing part is arranged in an array type using a hall device as a unit cell and the pulse-sensing part array is packaged to correspond to "Chon", "Gwan" and "Cheok" regions.

8. The pulsimeter sensor of claim 7,
wherein the pulse-sensing part array is formed by arranging arbitrary M×N unit cells at the each region on one semiconductor substrate and making a package.

9. The pulsimeter sensor of claim 7,
wherein the pulse-sensing part array comprises 10~18 unit cells per the each region.

10. The pulsimeter sensor of claim 7,
wherein the spatial part further comprises a space keeping member which connects the pulse-sensing part edge to the skin-contacting part edge and put a predetermined distance between the pulse-sensing part and the skin-contacting part.

11. The pulsimeter sensor of claim 10,
wherein the space keeping member is 1~3mm long.

12. The pulsimeter sensor of claim 7,
wherein the pulse-sensing part comprises a voltage detecting circuit for a hall voltage detected from the each hall device.

13. The pulsimeter sensor of claim 12,
wherein the voltage detecting circuit comprises a differential circuit.

14. The pulsimeter sensor of claim 13,
wherein the voltage detecting circuit further comprises a noise filter, a signal amplifier and an output attenuator, it has a plurality of channels, and the number of the channels is as many as the number of hall devices inside the pulse-sensing part.

15. The pulsimeter sensor of claim 14,
wherein the pulse-sensing part further comprises:
a multiplexer which receives multi-signals from the voltage detecting circuit and selects one signal;
a microprocessor which controls the multiplexer in such a way that the microprocessor receives each signal from the multiplexer, makes it a packet with a predetermined resolution, and transfers it; and
a communication driver which transfers the packet digital signal input by the microprocessor to an outer image processor.

16. The pulsimeter sensor of claim 7,
wherein to the skin-contacting part, a pressure sensor is adhered separately from the magnetic materials.

17. The pulsimeter sensor of claim 2,
wherein the pulse-sensing part is arranged in an array type using a hall device as a unit cell and the pulse-sensing part array is packaged to correspond to "Chon", "Gwan" and "Cheok" regions.

18. The pulsimeter sensor of claim 3,
wherein the pulse-sensing part is arranged in an array type using a hall device as a unit cell and the pulse-sensing part array is packaged to correspond to "Chon", "Gwan" and "Cheok" regions.

19. The pulsimeter sensor of claim 4,
wherein the pulse-sensing part is arranged in an array type using a hall device as a unit cell and the pulse-sensing part array is packaged to correspond to "Chon", "Gwan" and "Cheok" regions.

20. The pulsimeter sensor of claim 5,
wherein the pulse-sensing part is arranged in an array type using a hall device as a unit cell and the pulse-sensing part array is packaged to correspond to "Chon", "Gwan" and "Cheok" regions.

* * * * *